United States Patent [19]

Merger et al.

[11] Patent Number: 4,997,955

[45] Date of Patent: Mar. 5, 1991

[54] PREPARATION OF 1,1-DISUBSTITUTED ETHYLENE COMPOUNDS

[75] Inventors: Franz Merger; Joerg Liebe, both of Frankenthal; Werner Bertleff, Viernheim, all of Fed. Rep. of Germany

[73] Assignee: BASF Aktiengesellschaft, Ludwigshafen, Fed. Rep. of Germany

[21] Appl. No.: 205,341

[22] Filed: Jun. 10, 1988

[51] Int. Cl.$^5$ .................... C07C 45/27; C07C 67/42; C07D 207/263

[52] U.S. Cl. .................... 548/551; 560/190; 560/210; 560/212; 558/379; 558/382; 558/383; 558/330; 549/326; 549/62

[58] Field of Search ............... 548/551; 560/210, 190, 560/212; 568/330; 558/383, 379

[56] References Cited

U.S. PATENT DOCUMENTS

| | | | |
|---|---|---|---|
| 2,469,768 | 3/1949 | Redmar et al. | 560/212 |
| 2,819,296 | 1/1958 | Carnes et al. | 560/209 |
| 3,535,371 | 10/1970 | Wolf et al. | 560/210 |
| 3,642,843 | 2/1972 | Nemec et al. | 558/379 |
| 3,928,458 | 12/1975 | Hagemeyer, Jr. | 260/258 R |
| 4,336,403 | 6/1982 | Merger | 560/211 |

FOREIGN PATENT DOCUMENTS

| | | | |
|---|---|---|---|
| 0295553 | 12/1988 | European Pat. Off. | 560/210 |
| 3010968 | 10/1981 | Fed. Rep. of Germany | |
| 1586805 | 3/1981 | United Kingdom | |

OTHER PUBLICATIONS

J. Org. Chem., 37, 1256, (1972).
Kirk-Othmer, vol. 13, pp. 865-870, 3rd Edition.
E. C. Leonard, Vinyl and Diene Monomers, Part 1, Wiley-Interscience, New York, 1970, pp. 205-261.

Primary Examiner—David B. Springer
Attorney, Agent, or Firm—Keil & Weinkauf

[57] ABSTRACT

1,1-disubstituted ethylene compounds of the general formula I

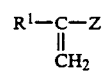

where Z is $COOR^2$, CN or $COR^3$, $R^1$ is an aliphatic, cycloalophatic, araliphatic, aromatic or heterocyclic radical which may be further substituted by functional groups which are inert under the reaction conditions, $R^2$ is an aliphatic, cycloaliphatic or araliphatic radical of 1 to 15 carbon atoms and $R^3$ is an aliphatic, cycloaliphatic or araliphatic radical of 1 to 15 carbon atoms which may be substituted by groups which are inert under the reaction conditions, and $R^1$ together with $R^2$ or $R^1$ together with $R^3$ may furthermore form an alkylene chain of 2 to 10 carbon atoms which may be substituted by groups which are inert under the reaction conditions, are prepared from a formyl compound of the general formula II

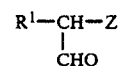

where Z, $R^1$, $R^2$ and $R^3$ have the above meanings, by a process in which the reaction is carried out in the presence of formaldehyde or paraformaldehyde and (a) a $C_1$-$C_{12}$-alkanol or
(b) a mixture of a $C_1$-$C_{12}$-alkanol and water or
(c) with water in the presence of a secondary amine and a protic acid at from 0° to 200° C.

10 Claims, No Drawings

PREPARATION OF 1,1-DISUBSTITUTED ETHYLENE COMPOUNDS

The present invention relates to a novel and improved process for the preparation of 1,1-disubstituted ethylene compounds.

The preparation of 2-substituted acrylates from 2-formylcarboxylates by hydrogenation of the formyl group to the hydroxyl group and subsequent elimination of water is known (e.g. British Patent 1,586,805 and P. E. Pfeffer et al., J. Org. Chem. 37 (1972), 1256). Similarly, 2formylnitriles or α-formylketones can be converted into the corresponding unsaturated compounds. However, two reaction steps are required here, and the yields are not very high.

$$\underset{\substack{|\\CH_2=C-CH_2-COOR''}}{COOR'}$$

are produced industrially from itaconic acid and aLcohols in the presence of acids by a classical esterification method.

Itaconic acid is now produced biochemically by fermentation of carbohydrates (molasses). The biochemical synthesis is technically very complicated, leads to low space-time yields and is therefore very expensive. To date, however, it has been preferred to a number of chemical syntheses, such as dry distillation of citric acid, oxidation of isoprene or mesityl oxide to citraconic acid with subsequent isomerization, carboxylation of acetylene derivatives, e.g. propargyl chloride or butynoates, or condensation of succinates or succinic anhydride with formaldehyde to give citraconic acid with subsequent isomerization, which cannot be carried out economically since, for example, they comprise many stages, give unsatisfactory yields and employ starting materials which are not readily accessible (cf. Kirk-Othmer, Vol. 13, pages 865-870; B. E. Tate, Itaconic Acid, Itaconic Esters and Related Compounds, in E. C. Leonard, Vinyl and Diene Monomers, Part 1, Wiley Interscience, New York 1970, pages 205-261).

It is an object of the present invention to provide a novel and improved process for the preparation of 1,1-disubstituted ethylene compounds from formyl compounds and to overcome the disadvantages of the known processes.

We have found that this object is achieved by a process for the preparation of 1,1-disubstituted ethylene compounds of the general formula I $$\underset{\substack{\|\\CH_2}}{R^1-C-Z} \qquad (I)$$

where Z is COOR$^2$, CN or COR$^3$, R$^1$ is an aliphatic, cycloaliphatic, araliphatic, aromatic or heterocyclic radical which may be further substituted by functional groups which are inert under the reaction conditions, R$^2$ is an aliphatic, cycloaliphatic or araliphatic radical of 1 to 15 carbon atoms and R$^3$ is an aliphatic, cycloaliphatic or araliphatic radical of 1 to 15 carbon atoms which may furthermore be substituted by groups which are inert under the reaction conditions, and R$^1$ together with R$^2$ or R$^1$ together with R$^3$ may furthermore form an alkylene chain of 2 to 10 carbon atoms which may be substituted by groups which are inert under the reaction conditions, from a formyl compound of the general formula II $$\underset{\substack{|\\CHO}}{R^1-CH-Z} \qquad (II)$$

where Z, R$^1$, R$^2$ and R$^3$ have the above meanings, wherein the reaction is carried out in the presence of formaldehyde or paraformaldehyde and
  (a) a C$_1$–C$_{12}$-alkanol or
  (b) a mixture of a C$_1$–C$_{12}$-alkanol and water or
  (c) with water in the presence of a secondary amine
and of a protic acid
at from 0° to 200° C.

For example, where methyl 2-formylpropionate is used, the reaction can be represented by the following equation:

$$CH_3-\underset{\substack{|\\CHO}}{CH}-COOCH_3 + H_2CO + CH_3OH$$

$$\Big\downarrow -H_2O$$

$$CH_3-\underset{\substack{\|\\CH_2}}{C}-COOCH_3 \; + \; HCOOCH_3$$

and where dimethyl 2-formylsuccinate is used, the reaction may be represented by the following equation:

$$OHC-\underset{\substack{|\\}}{CH}\overset{COOCH_3}{\phantom{|}}-CH_2-COOCH_3 + H_2C=O +$$

$$CH_3OH \xrightarrow[-H_2O]{+H^\oplus, HNR_2}$$

$$H_2C=\underset{\substack{|\\}}{C}\overset{COOCH_3}{\phantom{|}}-CH_2-COOCH_3 + HCCOCH_3$$

The formyl compounds II required for the reaction can be obtained by a known method, for example by ester condensation of carboxylates, of carboxylic acid nitriles or of ketones with alkyl formates or, preferably, by hydroformylation of α, β-unsaturated carboxylates, carboxylic acid nitriles or ketones.

Preference is given to using 2-formylcarboxylates, 2-formylcarboxylic acid nitriles or 2-formylketones of the general formula II where Z is COOR$^2$, CN or COR$^3$, R$^1$ is alkyl of 1 to 12, in particular 1 to 8, carbon atoms, alkenyl of 2 to 12 carbon atoms, oxaalkyl of 1 to 12 carbon atoms and 1 to 5 oxygen atoms, cycloalkyl of 5 to carbon atoms, aralkyl of 7 to 12 carbon atoms, aryl of to 12 carbon atoms or a heterocyclic radical of 2 to 6 carbon atoms and 1 to 3 nitrogen, oxygen or sulfur atoms, R$^2$ is alkyl of 1 to 6 carbon atoms, cycloalkyl of 5 to 8 carbon atoms or aralkyl of 7 to 12 carbon atoms, R$^3$ is alkyl of 1 to 12, in particular 1 to 8, carbon atoms, alkenyl of 2 to 12 carbon atoms, oxaalkyl of 1 to 12 carbon atoms and 1 to 5 oxygen atoms, cycloalkyl of 5 to 8 carbon atoms, aralkyl of 7 to 12 carbon atoms, aryl of 6 to 12 carbon atoms, and R$^1$ together with R$^2$ or R$^1$ together with R$^3$ may furthermore form an alkylene chain of 2 to 8 carbon atoms which may be substituted by groups which are inert under the reaction conditions. The abovementioned radicals may be further substituted by additional groups which are inert under the reaction conditions, in particular alkyl, alkoxy, halogen, ester, nitrile or tert-amino. Particularly preferred starting materials are alkyl 2-formylpropionates, alkyl 2-formylbutyrates and alkyl 2-formylsuccinates.

Examples of starting materials are the following: methyl 2-formylpropionate, ethyl 2-formylpropionate, methyl 2-formylbutyrate, ethyl 2-formylbutyrate and dimethyl, diethyl, dipropyl, diisopropyl, dibutyl, dihexyl, dioctyl, didecyl, diallyl, di-(2-methoxyethyl), dicyclohexyl, ethylmethyl, butylmethyl and dibenzyl 2-formylsuccinate.

Formaldehyde may be used in aqueous form, preferably as a 20-60% strength aqueous solution, in a form having a low water content, for example in solution in a mixture of water, a $C_1$-$C_8$-alkanol and, if required, a solvent, or in anhydrous form, for example in gaseous form, dissolved in a $C_1$-$C_8$-alkanol in the presence or absence of a solvent, or in the form of paraformaldehyde. The molar ratio of starting material II to formaldehyde is advantageously from 0.5:1 to 2.0:1, although molar ratios outside this range are also possible.

Suitable alcohols are $C_1$-$C_{12}$-alkanols, preferably $C_1$-$C_8$-alkanols, particularly preferably methanol. Polyhydric alcohols, e.g. glycol or glycerol, may also be used. The molar ratio of starting material II to the alkanol is in general from 1:1 to 1:50, preferably from 1:2 to 1:25, in particular from 1:2 to 1:15. Molar ratios outside this range are, however, also possible.

Surprisingly, the reaction takes place under conditions which are so mild that it is possible to avoid transesterification when using alkanols which do not correspond to the ester alcohol $R^2$-OH.

Instead of the alcohols, it is also possible to use corresponding amounts of water or mixtures of alcohols and water, in particular water-soluble alcohols with water.

In a preferred embodiment of the novel process, the alkanol required for the reaction, or water, is used in excess, in which case it also serves as the solvent. However, it is also possible to use other solvents in the reaction. Examples of suitable solvents are cyclic ethers, such as tetrahydrofuran or dioxane.

Suitable protic acids are inorganic or organic acids; instead of a monobasic acid, it is also possible to use equivalent amounts of polybasic acids. Acidic ion exchanger resins are also suitable. Examples of suitable acids are: aliphatic monocarboxylic acids of 1 to 10 carbon atoms, e.g. acetic acid, propionic acid, butyric acid, valeric acid, hexanoic acid, heptanoic acid, octanoic acid or decanoic acid; aromatic carboxylic acids, e.g. benzoic acid; acidic ion exchangers containing carboxyl groups or sulfo groups; aliphatic and aromatic sulfonic acids, e.g. methanesulfonic acid, benzenesulfonic acid or p-toluenesulfonic acid; aliphatic dicarboxylic acids of 2 to 6 carbon atoms, e.g. oxalic acid, succinic acid or adipic acid, and inorganic acids, e.g. sulfuric acid, phosphoric acid or hydrochloric acid. Aliphatic monocarboxylic acids of 2 to 5 carbon atoms are preferably used, acetic acid being particularly preferred.

The molar ratio of starting material II to protic acid may be from 1:0.005 to 1:1.5, preferably from 1:0.01 to 1:0.5, particularly preferably from 1:0.01 to 1:0.1 .

Suitable amines are the secondary amines conventionally used for Mannich reactions. Examples of suitable amines are those of the formula III

(III)

where $R^4$ and $R^5$ are identical or different and are each $C_1$-$C_{10}$-alkyl which may furthermore be substituted by inert groups, such as $C_1$-$C_4$-alkoxy or hydroxyl, or are each $C_5$- or $C_6$-cycloalkyl. Low molecular weight amines, in particular $C_2$-$C_{10}$-dialkylamines, such as dimethyl-, diethyl-, dipropyl- or dibutylamine or diethanolamine, are preferably used, dimethylamine being particularly preferred.

The molar ratio of starting material II to amine is, as a rule, from 1:0.005 to 1:1.5, preferably from 1:0.01 to 1:0.5, particularly preferably from 1:0.01 to 1:0.1.

The reaction can be carried out at from 0 to 200° C., preferably from 30° to 150° C., in particular from 40° to 100° C., under atmospheric, superatmospheric or reduced pressure.

The reaction is advantageously carried out as follows: the alcohol, if necessary the solvent, the protic acid and the amine are mixed, and the starting material II and formaldehyde, in gaseous form, dissolved in water, dissolved in the particular alkanol used or, where relevant, dissolved in a solvent or in the form of paraformaldehyde, are added in the course of from 0.01 to 10 hours. The mixture is heated to the reaction temperature, stirred for a further 1-100 hours at this temperature and then worked up. It is also possible for the mixture of solvent, alkanol, another solvent where relevant, protic acid and amine to be brought to the reaction temperature, and formaldehyde and the starting material II to be added at this temperature, or for all components to be mixed with one another at a low temperature (e.g. from 0° to 10° C.) and then brought to the reaction temperature. The conditions which are optimum for the particular starting materials used and the particular batch size can be determined by simple preliminary experiments.

Working up is carried out by a conventional method, for example by distillation and/or crystallization. If necessary, basic byproducts can be removed by extraction with an inorganic acid, e.g. aqueous sulfuric acid.

The desired 1,1-disubstituted ethylene compounds are obtained as the reaction products in very good yields, and the formates of the particular alkanol used, for example methyl formate where methanol is used, are obtained as useful byproducts. The alkyl formates can be utilized as such or can be cleaved by hydrolysis to give the alkanol, which can be recycled, and formic acid.

A particular advantage of the novel process is the purity of the resulting 1,1-disubstituted ethylene compounds, isomerization of the double bonds taking place to an insignificant extent, if at all. For example, in the preparation of dimethyl itaconate, neither dimethyl citraconate nor dimethyl mesaconate is detectable.

The 1,1-disubstituted ethylene compounds which can be prepared by the process, such as 2-substituted alkyl acrylates, acrylonitrile or α-methyleneketones, are useful starting materials for the preparation of plastics, molding materials, sections, coatings, lubricating oils, adhesives, textile assistants, plasticizers, etc. For example, the readily polymerizable itaconic diesters are used in the plastics industry, for example in conjunction with methacrylates and styrene. Itaconic diesters of higher alcohols serve as special plasticizers for synthetic resins based on polyvinyl chloride or for cellulose acetate and ethylcellulose.

The Examples which follow illustrate the invention.

EXAMPLE 1

A solution of 0.3 g acetic acid, 0.337 g of dimethylamine and 3.0 g of paraformaldehyde in 20 g of methanol is heated to 60° C. A solution of 11.6 g of methyl formylpropionate in 20 g of methanol is added dropwise in the course of 5 minutes, while stirring. Refluxing is then carried out for 7 hours. Quantitative gas chromatographic analysis of the solution shows that the yield of methyl methacrylate is 86.6%.

EXAMPLE 2

3.2 g of methanol, 0.328 g of a 36.5% strength aqueous formaldehyde solution, 0.0135 g of dimethylamine, 0.012 g of acetic acid and 0.464 g of methyl 2-formylpropionate are heated in a pressure-tight glass tube for 5 hours at 70° C. The yield of methyl methacrylate is 9%, determined by quantitative gas chromatographic analysis.

EXAMPLE 3

160 g of methanol, 0.842 g of dimethylamine, 0.75 g of acetic acid, 20.5 g of a 36.5% strength aqueous formaldehyde solution and 29.0 g of methyl 2-formylpropionate are stirred in a pressure-tight glass autoclave for 16 hours at 70° C. The methyl methacrylate yield determined by gas chromatography is 93.8% of theory. Methyl methacrylate can be separated off and isolated in pure form by distillation by a method known from the literature.

EXAMPLE 4

A mixture of 64 g of methanol, 0.34 g of dimethylamine, 0.3 g of acetic acid, 8.2 g of a 36.5% strength aqueous formaldehyde solution and 13.0 g of methyl 2-formylbutyrate is stirred for 69 hours at 65° C. and analyzed by gas chromatography. The yield of methyl -2-ethylacrylate is 82% of theory.

EXAMPLE 5

A mixture of 50 g of methanol, 0.34 g of dimethylamine, 0.3 g of acetic acid, 8.2 g of a 36.5% strength aqueous formaldehyde solution and 14.4 g of methyl 2-formylvalerate is stirred for 26 hours at 65° C. and analyzed by gas chromatography. The yield of methyl 2-(n-propyl)-acrylate is 72% of theory and 27% of starting material are still present.

EXAMPLE 6

A mixture of 20 g of methanol, 0.17 g of dimethylamine, 0.15 g of acetic acid, 4.2 g of a 37% strength aqueous formaldehyde solution and 13.0 g of methyl 2-formylprop-4-enoate is stirred for 26 hours at 65° C. and analyzed by gas chromatography. The yield of methyl 2allylacrylate is 7.5% of theory and 72% of starting material are still present.

EXAMPLE 7

3.0 g of paraformaldehyde and 17.8 g of methyl 2-formyl-2-phenylacetate are added to a solution of 0.34 g of dimethylamine and 0.3 g of acetic acid in 40 g of methanol. Refluxing is then carried out for 8 hours. The yield of methyl 2-phenylacrylate after distillation (100° C./0.3 mbar) is 78% of theory.

EXAMPLE 8

20 g of a 30% strength formaldehyde solution and 34.8 g of dimethyl 2-formylsuccinate are added to a solution of 9.0 g of oxalic acid and 14.6 g of diethylamine in 50 g of water. Heating is then carried out for 4 hours at 80° C. The organic phase which separates out contains dimethyl itaconate in a yield of 38%.

EXAMPLE 9

6.0 g of paraformaldehyde and 34.8 g of dimethyl 2-formylsuccinate are added to a solution of 14.8 g of propionic acid and 14.8 g of diethylamine in 160 g of methanol. The reaction mixture is stirred for 5 hours at 50° C. and then analyzed by quantitative gas chromatography. The yield of dimethyl itaconate is 85% of theory.

EXAMPLE 10

0.75 g of oxalic acid, 4.2 g of diethanolamine, 80 g of methanol, 6.0 g of paraformaldehyde and 34.8 g of dimethyl 2-formylsuccinate are used similarly to Example 8. After 12 hours at 50° C., the mixture is analyzed by gas chromatography. The yield of dimethyl itaconate is 65.4% of theory.

EXAMPLE 11

0.3 g of acetic acid, 0.675 g of dimethylamine, 40 g of methanol, 3.0 g of paraformaldehyde and 17.4 g of dimethyl 2-formylsuccinate are used similarly to Example 8. After 7 hours at 50° C., the mixture is analyzed by gas chromatography: the yield of dimethyl itaconate is 91.4% of theory.

EXAMPLE 12

0.3 g of acetic acid, 0.337 g of dimethylamine, 40 g of methanol, 3.0 g of paraformaldehyde and 17.4 g of dimethyl 2-formylsuccinate are used similarly to Example 8. After 7 hours at 50° C., the mixture is analyzed by gas chromatography: the yield of dimethyl itaconate is 99.0% of theory.

EXAMPLE 13

60 g of paraformaldehyde are added to a solution of 6.0 g of acetic acid and 6.75 g of dimethylamine in 800 g of methanol, after which 348 g of dimethyl 2-formylsuccinate are added dropwise in the course of 20 minutes. The mixture is stirred for 7 hours at 50° C. and allowed to cool, and methanol and methyl formate are distilled off. The residue is taken up in ethyl acetate and the solution is washed with 100 g of 10% strength sulfuric acid and distilled. 305 g of isomer-free dimethyl itaconate of boiling point 42°–43° C. under 0.3–0.4 mbar are obtained, corresponding to a yield of 96.4% of theory.

EXAMPLE 14

A stirred mixture of 20 g of ethanol, 0.337 g of dimethylamine, 0.3 g of acetic acid and 3 g of paraformaldehyde is heated to 50° C. and combined with a solution of 17.4 g of dimethyl 2-formylsuccinate in 20 g of ethanol. The mixture is refluxed for 6 hours and analyzed by gas chromatography. The yield of dimethyl itaconate is 91% of theory.

EXAMPLE 15

A mixture of 40 g of methanol, 0.337 g of dimethylamine, 0.3 g of acetic acid, 3 g of paraformaldehyde and 25.8 g of di-n-butyl 2-formylsuccinate is stirred under reflux for 4 hours. Gas chromatographic analysis indicates a yield of di-n-butyl itaconate of 98% of theory; there was no detectable transesterification to the methyl ester.

EXAMPLE 16

A mixture of 40 g of butanol, 0.337 g of dimethylamine, 0.3 g of acetic acid, 3 g of paraformaldehyde and 5.8 g of di-n-butyl 2-formylsuccinate is stirred for 4 hours at 65° C. and analyzed by gas chromatography. The yield of di-n-butyl itaconate is 82% of theory.

EXAMPLE 17

A mixture of 165 g of methanol, 1.39 g of dimethylamine, 1.24 g of acetic acid, 12.38 g of paraformaldehyde and 64 g of 2-formylbutyrolactone is stirred for 22 hours at 65° C. Methanol is distilled off and the residue is analyzed by gas chromatography. The yield of 2-methylenebutyrolactone is 72% of theory.

EXAMPLE 18

A mixture of 40 g of methanol, 0.34 g of dimethylamine, 0.3 g of acetic acid, 8.2 g of a 37% strength aqueous formaldehyde solution and 11.2 g of 2-formylcyclopentanone is stirred for 3 hours at 65° C. and analyzed by gas chromatography. The yield of 2-methylenecyclopentanone is 56% of theory.

EXAMPLE 19

A mixture of 40 g of methanol, 0.34 g of dimebhylamine, amine, 0.3 g of acetic acid, 8.2 g of a 37% strength aqueous formaldehyde solution and 13.8 g of 2-formylpropionitrile is stirred for 23 hours at 65° C. and analyzed by gas chromatography. The yield of methylacrylonitrile is 32% of theory and 67% of starting material are still present.

EXAMPLE 20

A mixture of 40 g of methanol, 0.34 g of dimethylamine, 0.3 g of acetic acid, 8.2 g of a 36.5% strength aqueous formaldehyde solution and 10.8 g of 2-formylsuccinodinitrile is stirred for 2 hours at 65° C. and analyzed by gas chromatography. The yield of itaconodinitrile is 9% of theory.

EXAMPLE 21

A mixture of 20 g of methanol, 0.17 g of dimethylamine, 0.15 g of acetic acid, 4.2 g of a 37% strength aqueous formaldehyde solution and 9.25 g of methyl 2-formyl-2-(2-pyrrolidon-1-yl)-acetate is refluxed for 2 hours and analyzed by gas chromatography. The yield of methyl 2-(2-pyrrolidon-1-yl)-acrylate is 20% of theory.

EXAMPLE 22

A mixture of 40 g of methanol, 0.34 g of dimethylamine, 0.3 g of acetic acid, 8.2 g of a 36.5% strength aqueous formaldehyde solution and 15.9 g of ethyl 2,Ndiformylaminoacetate is stirred for 20 hours at 65° C. and analyzed by gas chromatography. The yield of ethyl 2-(N-formylamino)-acrylate is 20% of theory.

What is claimed is:

1. A process for the preparation of a 1,1-disubstituted ethylene compound of the formula I

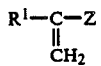

where Z is $COOR^2$, CN or $COR^3$, $R^1$ is an alkyl of 1 to 12 carbon atoms, alkenyl of 2 to 12 carbon atoms, oxaalkyl of 1 to 12 carbon atoms and 1 to 5 oxygen atoms, cycloalkyl of 5 to 8 carbon atoms, aralkyl of 7 to 12 carbon atoms, aryl of 6 to 12 carbon atoms, or a heterocyclic radical of 4 carbon atoms and 1 nitrogen, oxygen or sulfur atom having a carbonyl oxygen or sulfur, on a ring carbon adjacent to the ring hetero atom which may be further sutstituted by functional groups which are inert under the reaction conditions selected from the group consisting of alkyl, alkoxy, halogen, ester, nitrile and tert-amino groups, $R^2$ is an alkyl of 1 to 6 carbon atoms, cycloalkyl of 5 to 9 atoms or aralkyl of 7 to 12 carbon atoms and $R^3$ is an alkyl of 1 to 12 carbon atoms, alkenyl of 2 to 12 carbon atoms, oxaalkyl of 1 to 12 carbon atoms and 1 to 5 oxygen atoms, cycloalkyl of 5 to 8 carbon atoms, aralkyl of 7 to 12 carbon atoms or aryl of 6 to 12 carbon atoms which may be substituted by groups which are inert under the reaction conditions selected from the group condsisting of alkyl, alkoxy, halogen, ester, nitrile and tert-amino groups, and $R^1$ together with $R^2$ or $R^1$ together with $R^3$ may furthermore form an alkylene chain of 2 to 10 carbon atoms which may be substituted by groups which are inert under the reaction conditions selected from the group consisting of alkyl, alkoxy, halogen, ester, nitrole and tert-amino groups, from a formyl compound of the formula II

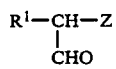

where Z, $R^1$, $R^2$ and $R^3$ have the above meanings, wherein the reaction is carried out in the presence of formaldehyde or paraformaldehyde and
(a) a $C_1$–$C_{12}$-alkanol or
(b) a mixture of a $C_1$–$C_{12}$-alkanol and water or
(c) with water
in the presence of a secondary amine and of protic acid at from 0° to 200° C.

2. The process of claim 1, wherein the reaction is carried out in the presence of from 0.5 to 2 moles of formaldehyde per mole of formyl compound II.

3. The process of claim 1, wherein the reaction is carried out in a $C_1$–$C_8$-alkanol.

4. The process of claim 1, wherein the reaction is carried out in methanol.

5. The process of claim 1, wherein the reaction is carried out in from 1 to 50 moles of alkanol per mole of formyl compound II.

6. The process of claim 1, wherein the reaction is carried out in the presence of an aliphatic monocarboxylic acid of 2 to 5 carbon atoms as the protic acid.

7. The process of claim 1, wherein the reaction is carried out in the presence of from 0.005 to 1.5 moles of a protic acid per mole of formyl compound II.

8. The process of claim 1, wherein the reaction is carried out in the presence of from 0.005 to 1.5 moles of a C2-C10-dialkylamine per mole of formyl compound II.

9. The process of claim 1 wherein the formyl compound of formula II used as the starting material is selected from the group consisting of alkyl 2-formylpropionates, alkyl 2-formylbutyrates and alkyl 2-formyl succinates.

10. The process of claim 1 wherein the formyl compound of formula II used as the starting material is selected from the group consisting of methyl 2-formylpropionate, ethyl 2-formylpropionate, methyl 2-formylbutyrate, ethyl 2-formylbutyrate and dimethyl, diethyl, dipropyl, diisopropyl, dibutyl, dihexyl, dioctyl, didecyl, diallyl, di0(b 2-methoxyethyl), dicyclohexyl, ethylmethyl, butylmethyl and dibenzyl 2-formylsuccinate.

* * * * *

UNITED STATES PATENT AND TRADEMARK OFFICE
CERTIFICATE OF CORRECTION

PATENT NO. : 4,997,955

DATED : March 5, 1991

INVENTOR(S) : Frank MERGER et al.

It is certified that error appears in the above-identified patent and that said Letters Patent is hereby corrected as shown below:

On the Cover Page:

Please insert

-- [30]  Foreign Application Priority Data
June 13, 1987   [DE]  Fed. Rep. of Germany ........ 3719873--.

Signed and Sealed this

First Day of December, 1992

Attest:

DOUGLAS B. COMER

Attesting Officer

Acting Commissioner of Patents and Trademarks